(12) United States Patent
Fabien

(10) Patent No.: US 12,716,762 B2
(45) Date of Patent: Aug. 25, 2026

(54) DOSE COUNTER FOR A DEVICE FOR DISPENSING A FLUID OR POWDER PRODUCT

(71) Applicant: APTAR FRANCE SAS, Le Neubourg (FR)

(72) Inventor: David Fabien, Saint Renan (FR)

(73) Assignee: APTAR FRANCE SAS, Le Neubourg (FR)

( * ) Notice: Subject to any disclaimer, the term of this patent is extended or adjusted under 35 U.S.C. 154(b) by 166 days.

(21) Appl. No.: 18/699,657

(22) PCT Filed: Oct. 20, 2022

(86) PCT No.: PCT/FR2022/051978
§ 371 (c)(1),
(2) Date: Apr. 9, 2024

(87) PCT Pub. No.: WO2023/067283
PCT Pub. Date: Apr. 27, 2023

(65) Prior Publication Data

US 2024/0410734 A1 Dec. 12, 2024

(30) Foreign Application Priority Data

Oct. 22, 2021 (FR) ....................................... 2111266

(51) Int. Cl.
*G01F 13/00* (2006.01)
*A61M 5/315* (2006.01)

(52) U.S. Cl.
CPC ......... *G01F 13/008* (2013.01); *A61M 5/3155* (2013.01)

(58) Field of Classification Search
CPC . G01F 13/008; A61M 5/3155; A61M 15/009; A61M 15/0075; G06M 1/26; G06M 1/248
See application file for complete search history.

(56) References Cited

U.S. PATENT DOCUMENTS 6,446,627 B1 * 9/2002 Bowman ............... G06M 1/083 128/200.23
2011/0266306 A1 * 11/2011 Laut .................... A61M 15/009 222/38
2012/0234317 A1 * 9/2012 Stuart ................ A61M 15/009 128/200.23

FOREIGN PATENT DOCUMENTS

DE 10 2006 040194 A1 3/2008
FR 2 873 808 A1 2/2006
FR 2 944 707 A1 10/2010

OTHER PUBLICATIONS

International Search Report issued Feb. 6, 2023 in International Application No. PCT/FR2022/051978.

(Continued)

*Primary Examiner* — Donnell A Long
(74) *Attorney, Agent, or Firm* — Sughrue Mion, PLLC

(57) ABSTRACT

A counter having an actuating element (20) and a counting element (30) with toothing (32), the actuating element axially movable along an axis (X) between a rest position and an actuation position, the counting element mounted to rotate on an axis perpendicular to the axis (X). The actuating element has a first flexible tab (21) engaging the toothing to rotate the counting element in a counting direction when the actuating element moves into its actuation position, and a second flexible tab (22) engaging the toothing to rotate the counting element in the counting direction when the actuation element returns to its rest position. The first and second flexible tabs are resiliently biased radially inward into contact with the first toothing. The counter has a stop element (19) which engages the second flexible tab limiting radially inward movement thereof when the actuating element moves into and out of its actuation position.

17 Claims, 9 Drawing Sheets

(56) References Cited

OTHER PUBLICATIONS

International Preliminary Report on Patentability (with translation of Written Opinion) dated Apr. 23, 2024, issued in International Application No. PCT/FR2022/051978.

* cited by examiner

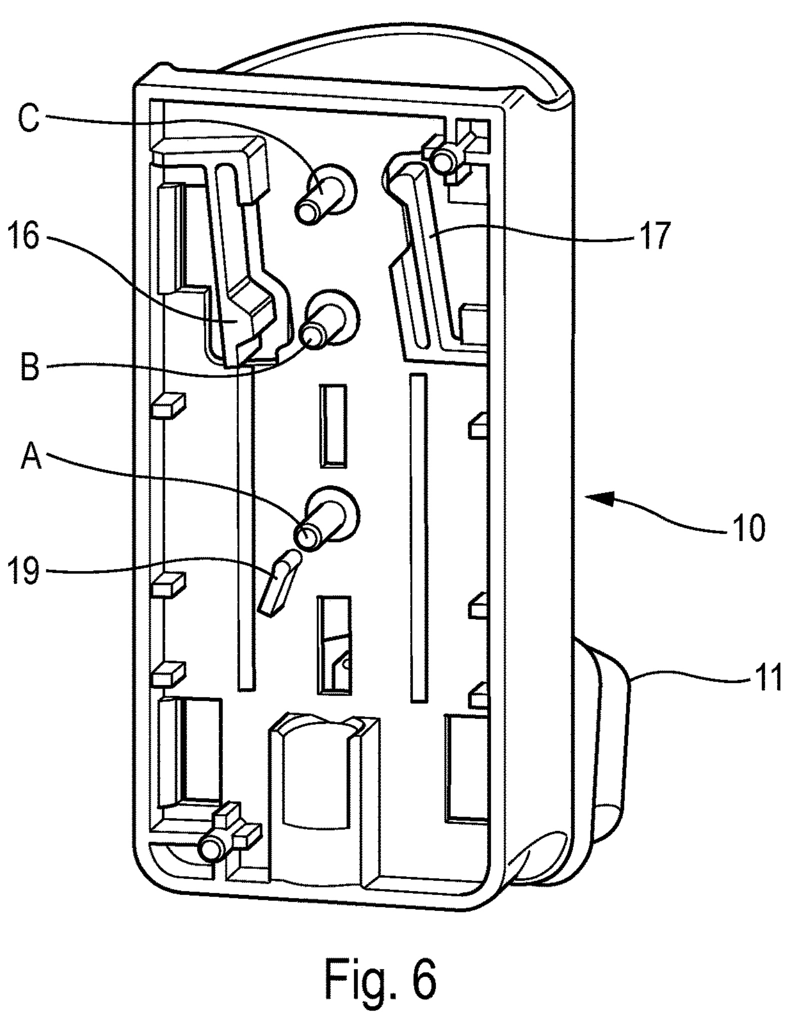
Fig. 6
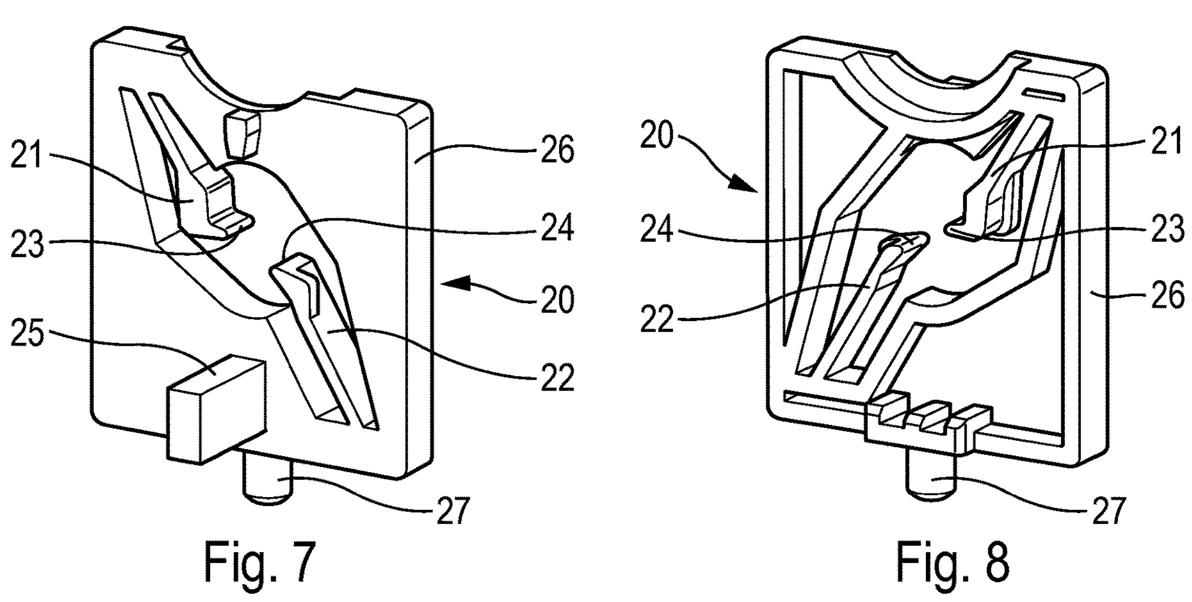
Fig. 7
Fig. 8

50
1
10
16
17
41
40
51
30
190
31
20
5

40
43
50
1
10
17
16
52
21
32
26
22
30
19
20
5

50
56
1
10
17
52
16
40
33
42
30
20
5

32x
32
A
32b
23
21
24
22
19
32y
32a
20

16
B
C
40
33
30
42

50
C
56
17
40
B
43
52
20

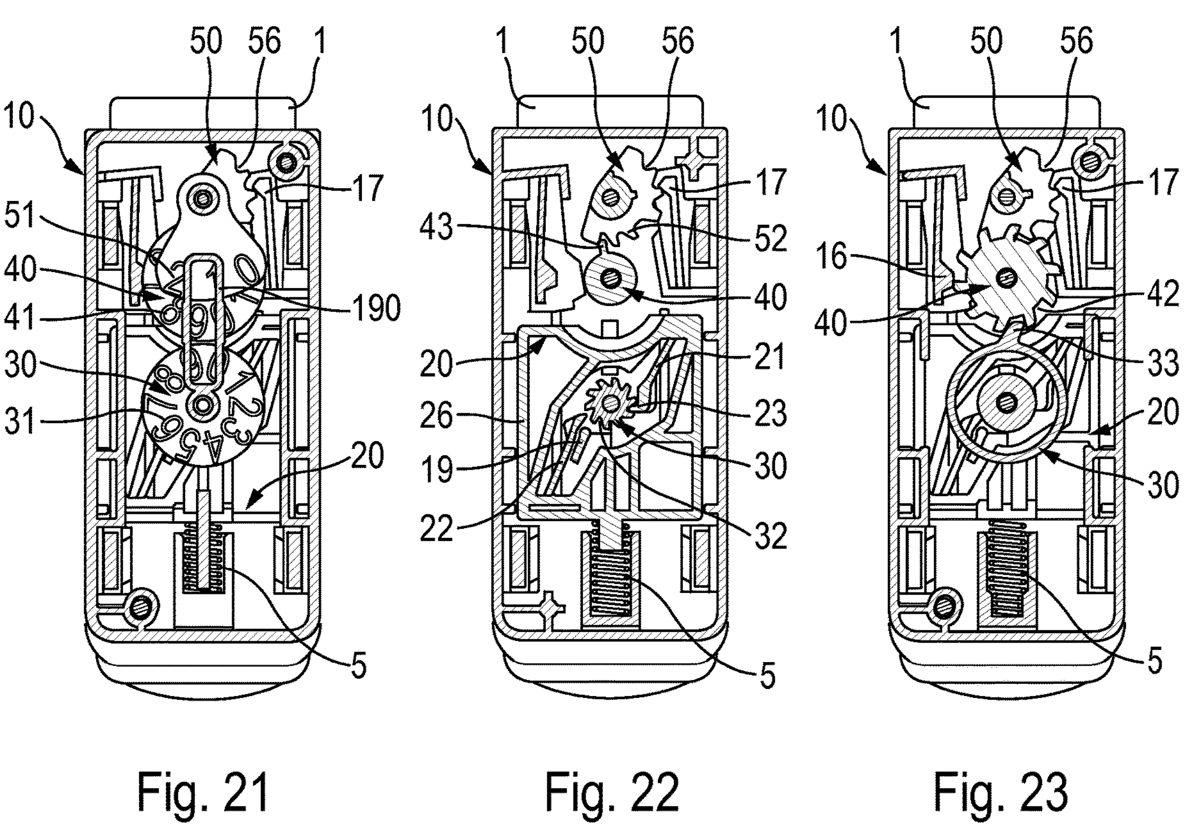
Fig. 21
Fig. 22
Fig. 23
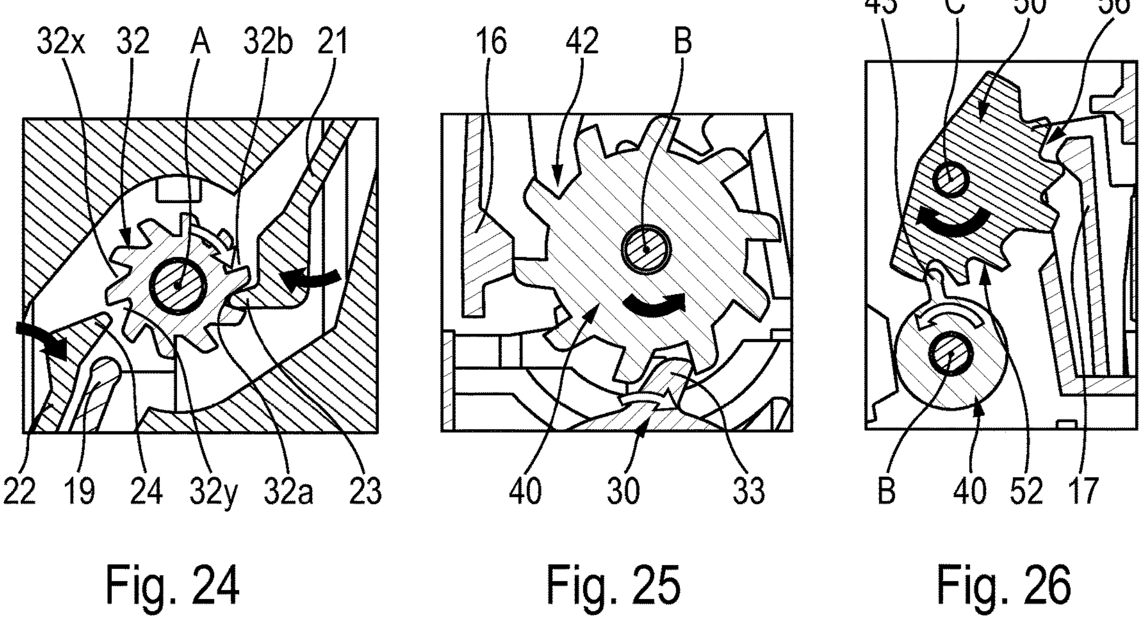
Fig. 24
Fig. 25
Fig. 26

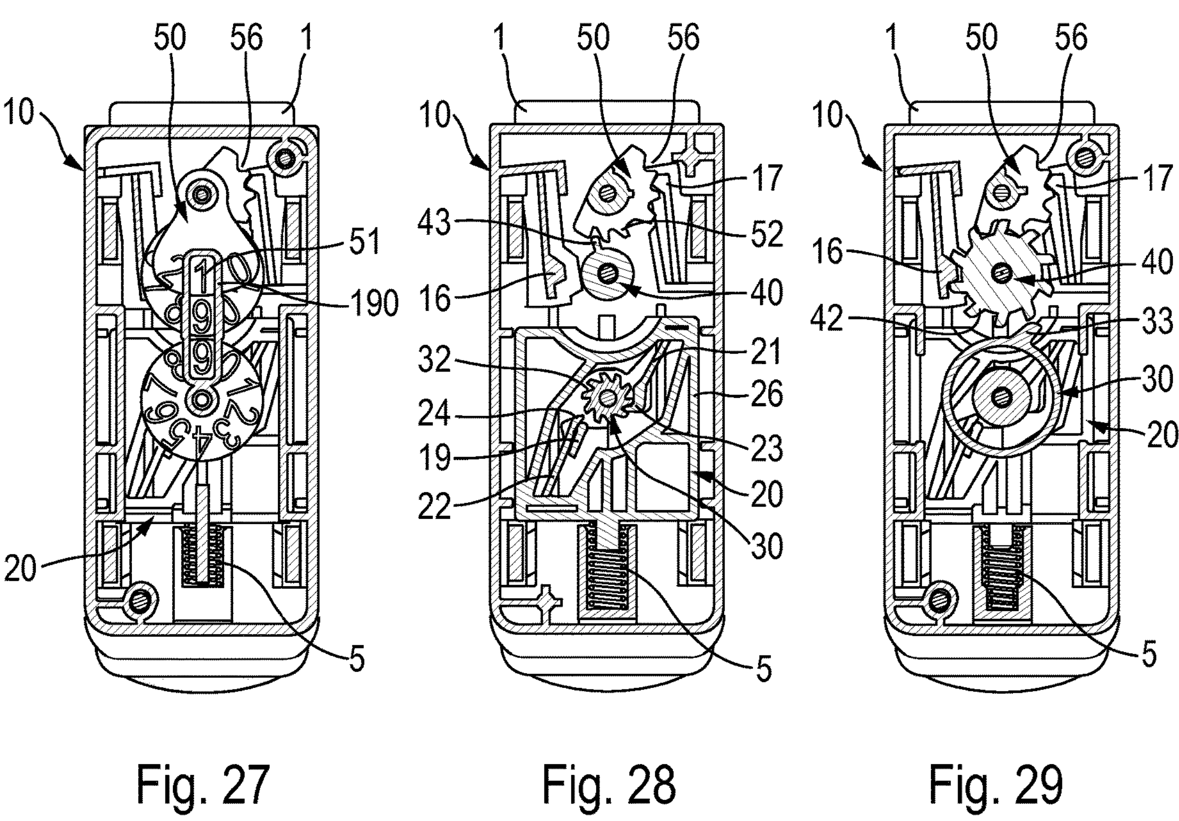
Fig. 27
Fig. 28
Fig. 29
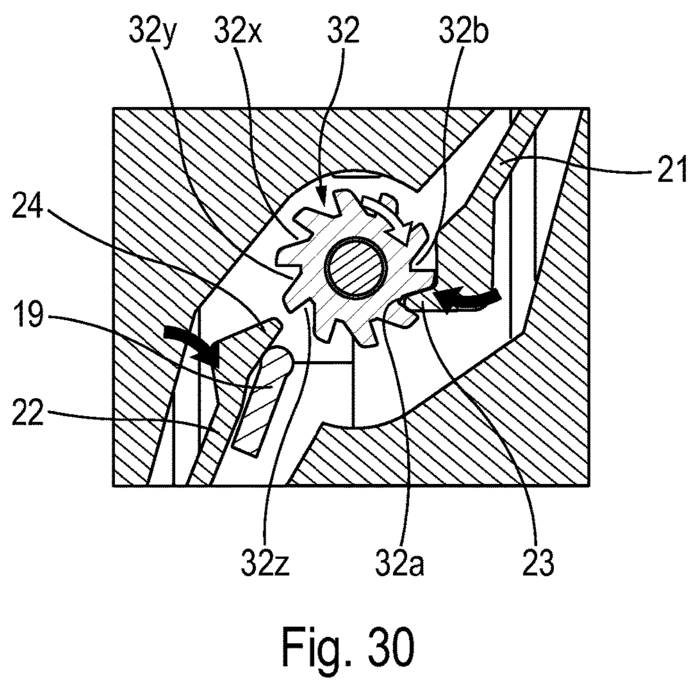
Fig. 30

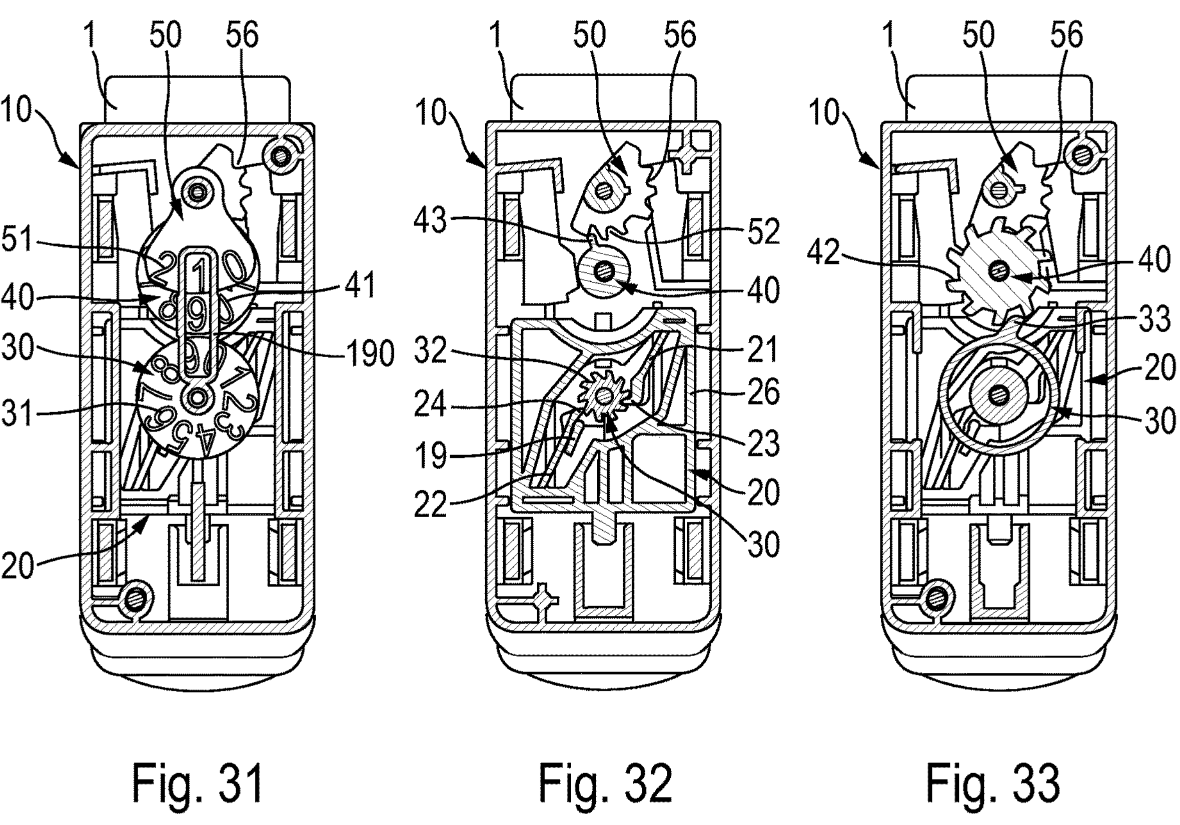
1
50
56
10
51
40
41
30
190
31
20
43
52
32
21
24
26
19
23
22
42
33
Fig. 31
Fig. 32
Fig. 33
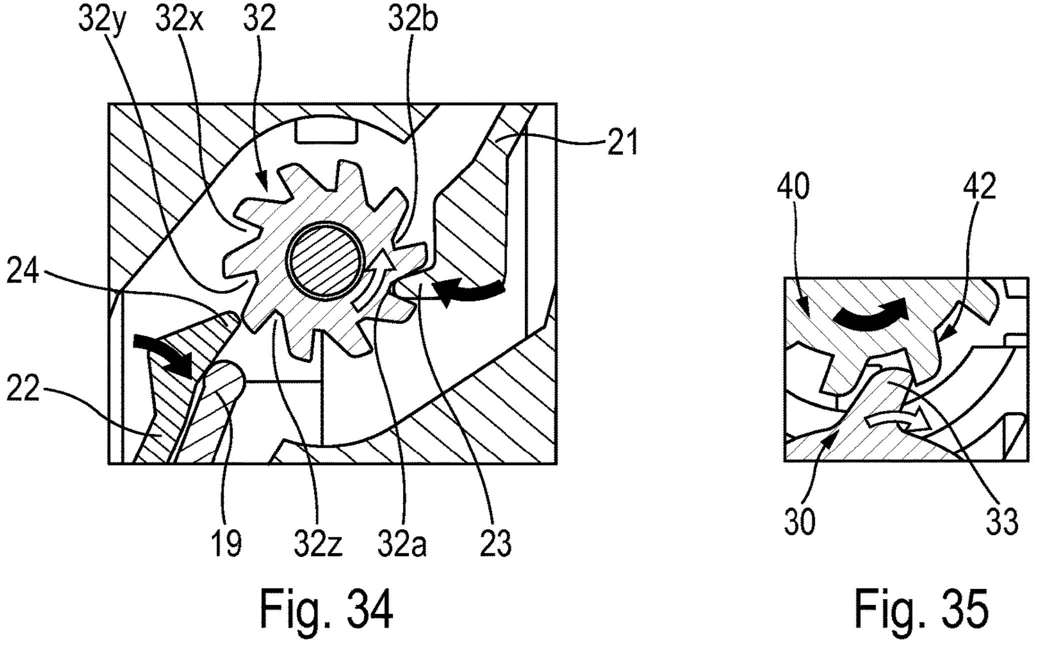
32y
32x
32
32b
21
24
22
19
32z
32a
23
Fig. 34
40
42
30
33
Fig. 35

DOSE COUNTER FOR A DEVICE FOR DISPENSING A FLUID OR POWDER PRODUCT

CROSS-REFERENCE TO RELATED APPLICATIONS

This is a National Stage of International Application No. PCT/FR2022/051978 filed Oct. 20, 2022, claiming priority based on French Patent Application No. 2111266 filed Oct. 22, 2021.

The present invention relates to a dose counter to indicate to the user, the number of doses dispensed or remaining to be dispensed from a device for dispensing a fluid or powder product.

Using counters is well-known in the field of fluid product dispensers, in particular, in the pharmaceutical field. In particular, when these counters are used with MDI (Metered Dose Inhaler)-type dispensing devices, wherein a reservoir containing the fluid product and a propellant is mounted so as to move in a body, the movement of said reservoir causing the actuation of a metering valve mounted on said reservoir to dispense a dose of product, several stresses rest on said counter. Thus, such counters can have risks of under-counting and/or over-counting. By under-counting, this means the fact of not counting a dose, while the fluid product has been expelled. Ultimately, this could result in a counter displaying that one or more dose (s) remain(s) to be dispensed, while the fluid product reservoir is empty. By over-counting, this means the fact of counting more than one dose during the expulsion of a fluid product dose. Ultimately, this could result in a counter displaying that no more doses remain to be dispensed, while the fluid product reservoir is not empty. In particular, to avoid any risk of under-counting, it is generally requested that the actuation of the counter is performed before the start of the actuation of the valve or of the pump, to avoid that a partial actuation dispenses a partial or complete dose which would not be counted by the counter. To do this, the maximum stroke of the actuation of the counter must be less than the minimum actuation stroke of the valve or of the pump, by considering the manufacturing tolerances of the parts constituting the counter and the valve or pump. The problem which is posed in this case, is that this stroke is generally very short and that the tolerances of the device tend to even further reduce effectively the available distance to perform this actuation. This generally requires the use of a complex mechanism to provide an operational and reliable counting.

Documents FR2944707A1, DE102006040194A1 and FR2873808A1 describe devices of the prior art.

The present invention aims to provide a dose counter for a device for dispensing a fluid or powder product which does not reproduce the abovementioned disadvantages.

The present invention aims, in particular, to provide such a counter which guarantees an actuation of the counter before the dose dispensing, independently of the length of the actuation stroke of the pump or of the valve used in the device.

The present invention also aims to provide such a counter which avoids any risk of under-counting.

The present invention also aims to provide such a counter which avoids any risk of over-counting.

The present invention also aims to provide such a counter which counts exactly the number of doses delivered, i.e. which counts exactly one dose upon each actuation.

The present invention also aims to provide such a counter which is simpler and therefore cheaper to manufacture and to assemble, and more operationally reliable.

The present invention therefore aims for a dose counter for a device for dispensing a fluid or powder product, comprising an actuation element and at least one first counting element provided with a first toothing defining a plurality of recesses, said actuation element being axially movable along an axis X between a rest position and an actuation position, by being resiliently biased towards its rest position by a resilient element, such as a spring, said first counting element being mounted so as to rotate on a first axis of rotation A perpendicular to said axis X, said actuation element comprising two flexible tabs, a first flexible tab engaging with said first toothing to rotate said first counting element in a counting direction when said actuation element moves from its rest position to its actuation position, and a second flexible tab engaging with said first toothing to rotate said first counting element also in said counting direction, when said actuation element returns from its actuation position to its rest position, said first and second flexible tabs being disposed radially outside of said first toothing and being resiliently biased radially inward into contact with said first toothing, said counter comprising a stop element engaging with said second flexible tab to limit its radial movement inward when said actuation element moves into and out of its actuation position.

Advantageously, said stop element, during an actuation cycle of the counter, guides said second flexible tab from an initial recess to an immediately adjacent recess, by preventing said second flexible tab from passing directly into a non-adjacent recess, thus preventing an over-counting.

Advantageously, said stop element is disposed radially inside and axially below said second flexible tab.

Advantageously, said stop element is radially and axially inclined with respect to said movement axis of said actuation element.

Advantageously, said first and second flexible tabs each comprise a free end in the form of a tip or a tooth, oriented opposite.

Advantageously, said counter further comprises a second counting element provided with a second toothing, said first counting element comprising a first cam engaging upon each complete rotation of said first counting element with said second toothing to rotate said second counting element.

Advantageously, a first indexing tab engages with said second toothing to define and maintain the position of said second counting element between two actuations.

Advantageously, said counter further comprises a third counting element provided with a third toothing, said second counting element comprising a second cam engaging upon each complete rotation of said second counting element with said third toothing to rotate said third counting element.

Advantageously, a second indexing tab engages with a fourth toothing of said third counting element to define and maintain the position of said third counting element between two actuations.

Advantageously, said first counting element is a units wheel, comprising first indication means formed by the figures 0 to 9 and a first toothing comprising ten recesses adapted to engage with said first and second flexible tabs of said actuation element, said second counting element is a tens wheel, comprising second indication means formed by the figures 0 to 9 and a second toothing comprising ten recesses adapted to engage with said first cam of said first counting element, and said third counting element is a hundreds wheel, comprising third indication means, in particular formed by the figures 0 to 2, and a third toothing comprising, in particular, three recesses adapted to engage with said second cam of said second counting element.

Advantageously, said counter comprises a cover provided with a viewing window.

The present invention also aims for a device for dispensing a fluid or powder product comprising a reservoir, a dispensing member, such as a metering valve, mounted on said reservoir, and a body incorporating a dispensing orifice, said reservoir being axially movable in said body along an axis X to dispense the fluid or powder product, said device comprising a dose counter such as described above.

Advantageously, said counter is fixed laterally to said body, the actuation of said device being performed by an axial manual pressure of the user on the reservoir and the actuation of said counter being performed by said axial movement of said reservoir which engages with said actuation element of said counter.

Advantageously, a first part of the actuation cycle of the counter is performed before any dispensing of fluid or powder product, and a second part of the actuation cycle of the counter is performed after dispensing of fluid or powder product.

Advantageously, said first counting element rotates on a first axis of rotation A, said second counting element rotates on a second axis of rotation B and said third counting element rotates on a third axis of rotation C, said axes of rotation A, B, C being perpendicular to said axis X of movement of said reservoir, said axes of rotation A, B, C being formed by respective studs of said body.

Other features and advantages of the present invention will appear more clearly during the detailed description below, made in reference to the accompanying drawings, given as non-limiting examples, and wherein:

FIG. 6 is a perspective, schematic view of the main body of the device of FIG. 1;

FIGS. 7 and 8 are perspective, schematic views of the drive element, respectively from the front and from the rear;

FIGS. 21 to 23 are views similar to those of FIGS. 15 to 17, during the actuation stroke;

FIGS. 24 to 26 are views similar to those of FIGS. 18 to 20, during the actuation stroke;

FIGS. 27 to 29 are views similar to those of FIGS. 15 to 17, at the end of the actuation stroke;

FIG. 30 is a view similar to that of FIG. 18 at the end of the actuation stroke;

FIGS. 31 to 33 are views similar to those of FIGS. 15 to 17, during the return stroke;

FIGS. 34 and 35 are views similar to those of FIGS. 18 and 19 during the return stroke;

In the description below, the terms "axial" and "radial" refer to a respective axis, which is either the axis X of movement of the actuation element 20, or one of the axes A, B or C of rotation of the first, second or third counting elements 30, 40, 50. The terms "top" and "bottom" refer to the use position represented in FIGS. 4 and 15 to 41.

Figures 1, 2, 3:
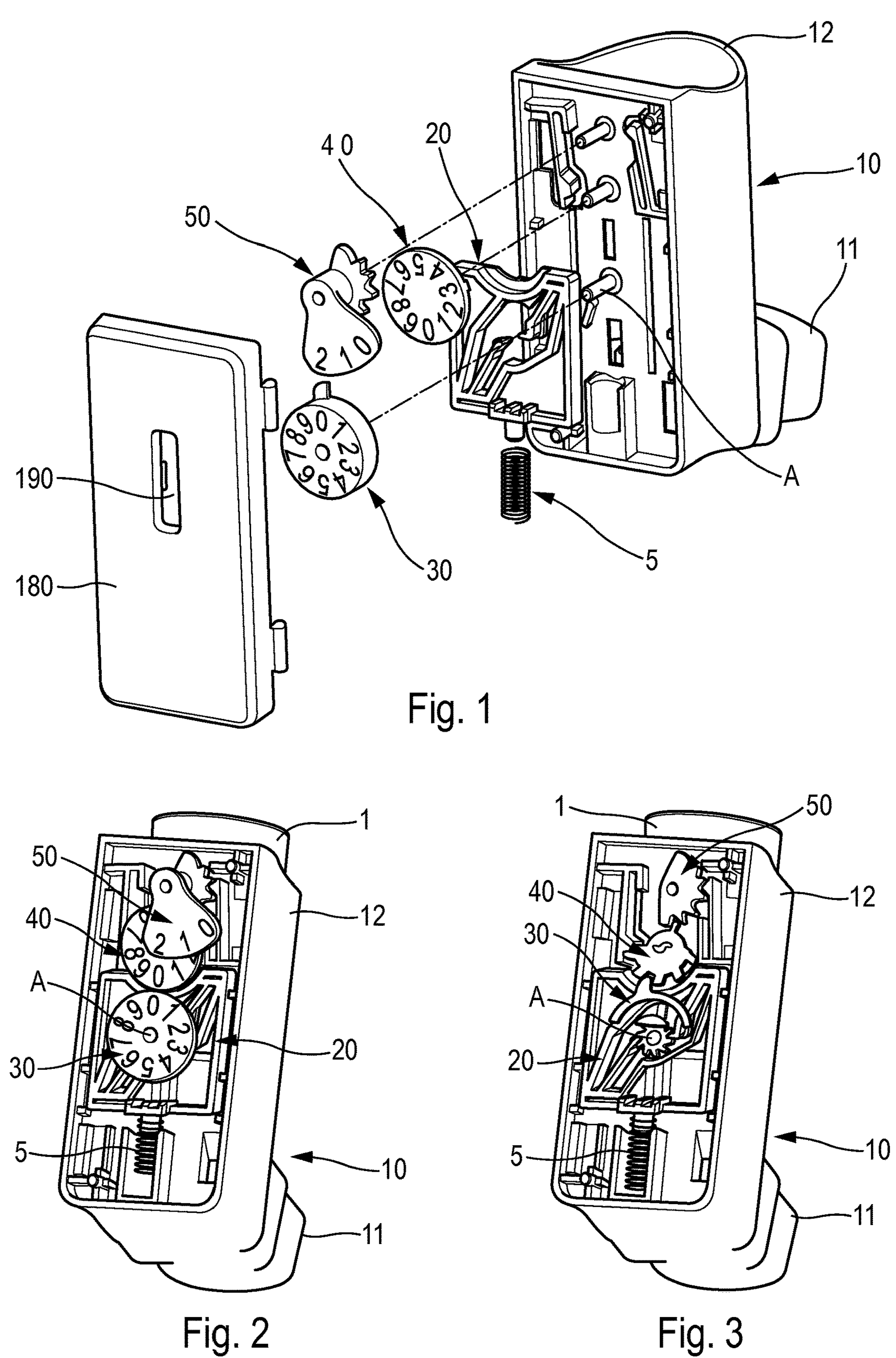
FIG. 1 is a perspective, exploded, schematic view of a device for dispensing a fluid product comprising a counter according to an advantageous embodiment of the present invention.
FIG. 2 is a cross-sectional, perspective, schematic view of the device of FIG. 1, showing the counter along a first cutting plane.
FIG. 3 is a view similar to that of FIG. 2, along another cutting plane.
Figure 4:
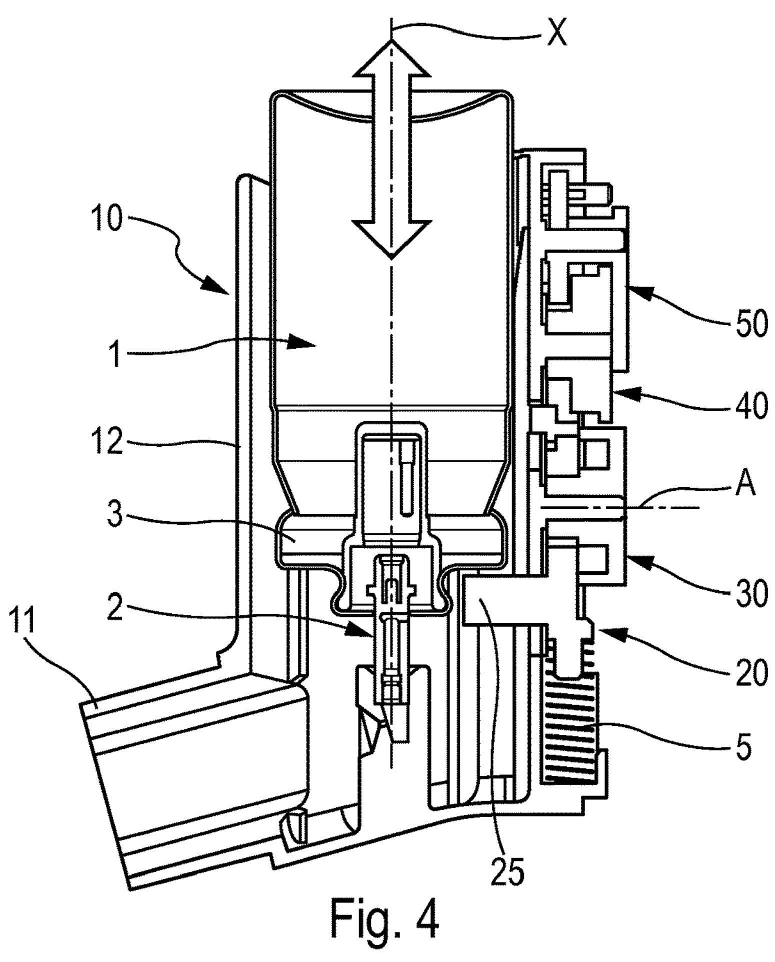
FIG. 4 is a cross-sectional, schematic view of the device of FIG. 1.
Figure 5:
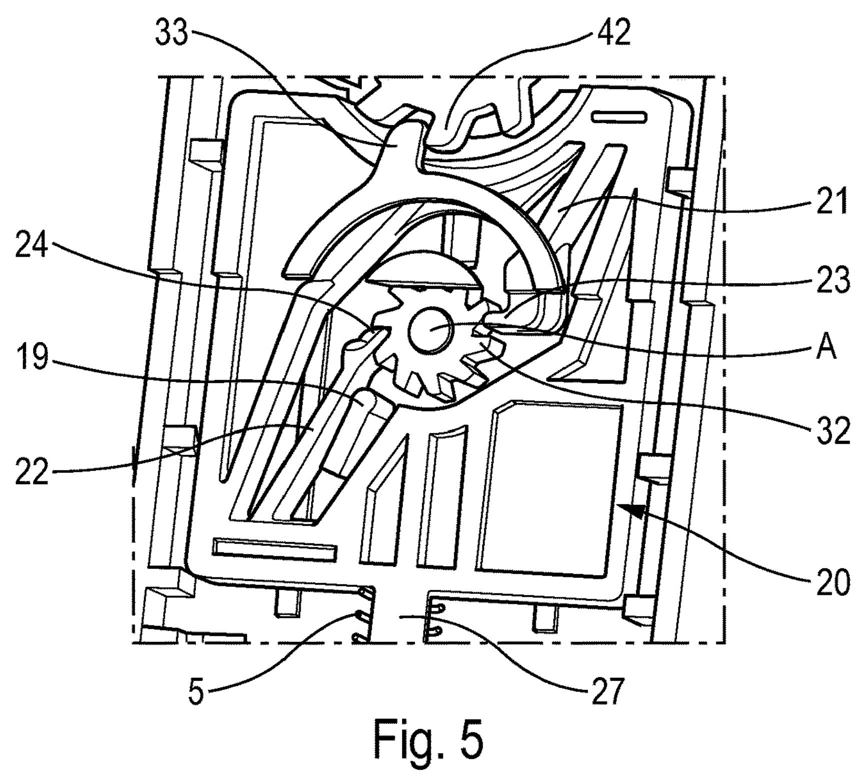
FIG. 5 is a cross-sectional, perspective, partial schematic view of a part of the counter of FIG. 1.

In reference to FIG. 1, a device for dispensing a fluid product comprising a dose counter is represented in an exploded view, which corresponds to a particular embodiment of the present invention. Naturally, this implementation is only one example of an embodiment and several elements could be achieved differently.

The device represented in FIG. 1 comprises a body 10 provided with a mouthpiece 11 and comprising a hollow sleeve 12 receiving a reservoir 1 on which a metering valve 2 is mounted by means of a fixing ring 3. The reservoir 1 is axially movable along an axis X in said hollow sleeve between a rest position and an actuation position, and is resiliently biased towards its rest position, generally by a return spring of said metering valve 2.

The counter comprises at least one first counting element 30, engaging with an actuation element 20. The actuation element 20 is axially movable in translation along an axis parallel to the axis X of movement of the reservoir 1 between a rest position, which can be seen in FIG. 16, and an actuation position, which can be seen in FIG. 28. The first counting element 30 is mounted so as to rotate on a first axis of rotation A perpendicular to said axis X of the reservoir 1. The actuation element 20 comprises drive means 21, 22 which transform the axial movement of the actuation element 20 into a rotary movement of the first counting element 30. A resilient element 5, such as a spring, resiliently biases the actuation element 20 to its rest position.

The first counting element 30 is a units wheel, and the counter can advantageously further comprise a second counting element 40 forming a tens wheel. In the embodiment represented in the drawings, there is also a third counting element 50 forming a hundreds wheel.

As can be seen in FIGS. 1 to 4, the counter is mounted laterally with respect to the body 10. The actuation element 20 comprises a projection 25 which is in contact with the reservoir 1 or with an element integral with said reservoir 1, such as the fixing ring 3. During an axial movement of said reservoir 1 in the hollow sleeve 12 of the body 10, the reservoir 1 moves this projection 25, which causes an axial movement of said actuation element 20.

The counter is assembled on the body 10, and a cover 180, provided with a viewing window 190, is provided to lock the assembly of the counter on the body 10.

According to the invention, the body 10 comprises a stop element 19 engaging with a movable part of the counter during the actuation, as will be described in detail below. Advantageously, the stop element 19 is formed by a projection radially and axially inclined with respect to the axis of movement of the actuation element 20.

The actuation element 20, represented in detail in FIGS. 7 and 8, comprises a base body 26 which supports two flexible tabs 21, 22 forming the drive means. The base body 26 also supports the projection 25. The first and second flexible tabs 21, 22 each comprise a free end 23, 24, advantageously in the form of tips or teeth, oriented opposite. An axial lug 27 can be provided to receive a spring 5 adapted to resiliently return the actuation element 20 from its actuation position to its rest position. In a variant to the spring 5 represented in the drawings, the counter could comprise one or more resilient blades to perform this return spring function.

Figure 9:
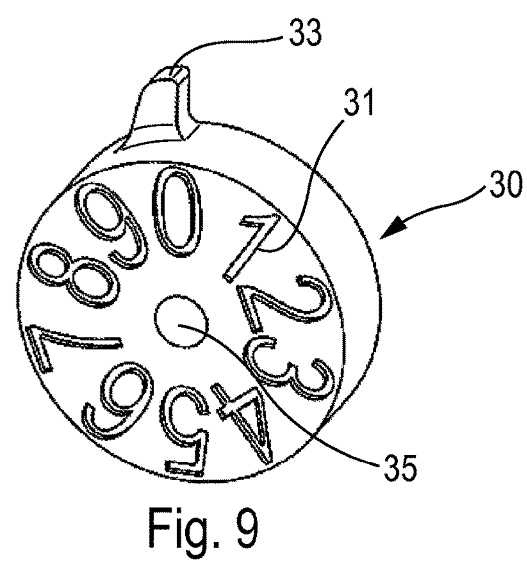
FIGS. 9 and 10 are perspective, schematic views of the units wheel, respectively from the front and from the rear.
Figure 10:
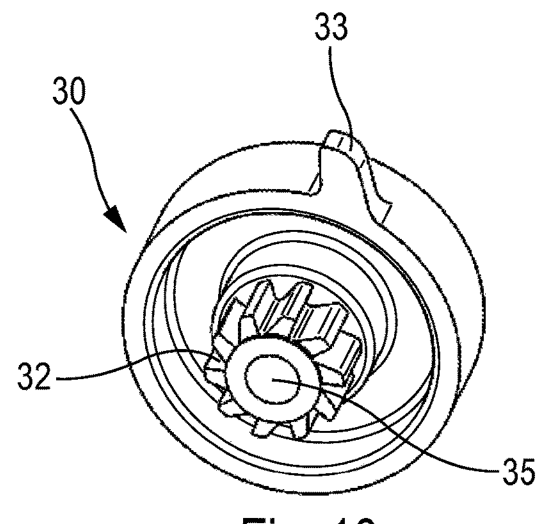

The first counting element 30, represented in detail in FIGS. 9 and 10, comprises, on one side, first indication means 31 intended to be visible through the viewing window 190 provided in the cover 180 of the counter, and on the other side, a first toothing 32 intended to engage with the flexible tabs 21, 22 of the actuation element 20. The first and second flexible tabs 21, 22 are disposed radially outside of said first toothing 32 and are radially biased inward into contact with said first toothing 32.

In the example represented, the first counting element 30 is a units wheel, and the first indication means 31 are therefore formed by the figures 0 to 9. Likewise, the first toothing 32 comprises ten teeth defining ten recesses adapted to engage with the free ends 23, 24 of the two flexible tabs 21, 22. Advantageously, each tooth of the first toothing 32 comprises a stop surface and an inclined surface which connects this stop surface to the stop surface of the directly adjacent tooth. The first counting element 30 comprises a central hole 35 which is inserted on a first stud of the body 10 forming the first axis of rotation A, such that the first counting element 30 rotates on said first axis of rotation A. When it is associated with a second counting element 40, the first counting element 30 comprises a first cam 33, which can be formed by a radial projection, as can be seen in FIGS. 9 and 10, and which is adapted to engage with the second counting element 40 upon each complete rotations, therefore every ten actuations in the example of the figures.

The first flexible tab 21 engages with said first toothing 32 of the first counting element 30 when the actuation element 20 is moved from its rest position to its actuation position. This has the consequence of rotating said first counting element 30 in a counting direction. The second flexible tab 22 engages with said first toothing 32 of the first counting element 30 to rotate said counting element 30 in this same counting direction when the actuation element 20 returns from its actuation position to its rest position. In other words, the actuation cycle of the counter is separated into two distinct parts, a first part produced when the actuation element 20 is moved from its rest position to its actuation position and a second part which is produced when the actuation element returns from its actuation position to its rest position.

Figure 11:
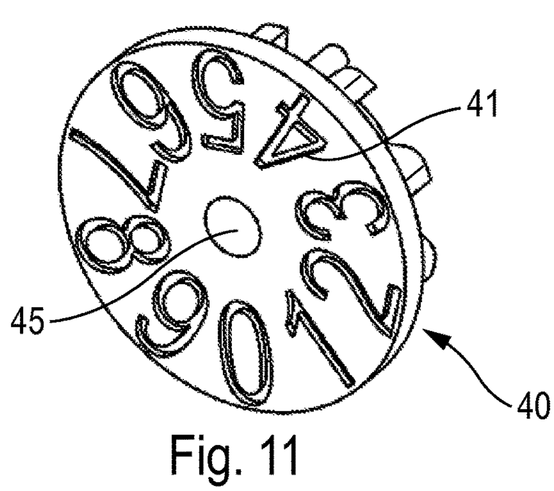
FIGS. 11 and 12 are perspective, schematic views of the tens wheel, respectively from the front and from the rear.
Figure 12:
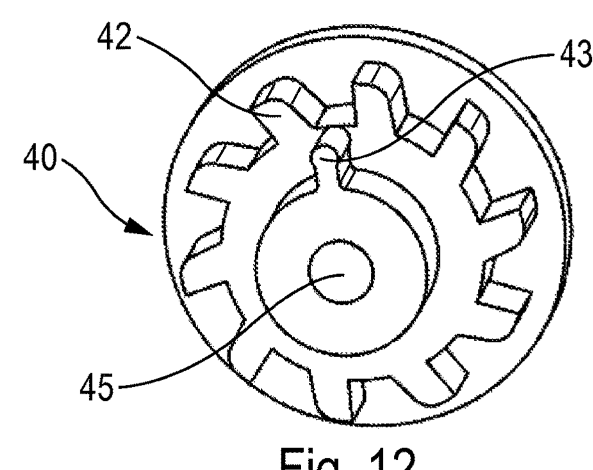

The second counting element 40, represented in detail in FIGS. 11 and 12, comprises on one side, second indication means 41 intended to be visible through the viewing window 190 of the counter, and on the other side, a second toothing 42 intended to engage with said first cam 33 of the first counting element 30, each time that the first counting element 30 has performed a complete rotation. In the example represented, the second counting element 40 is a tens wheel, and the second indication means 41 are therefore formed by the figures 0 to 9. Likewise, the second toothing 42 comprises ten teeth defining ten recesses adapted to engage with said first cam 33. Advantageously, each tooth of the second toothing 42 comprises a stop surface and an inclined surface which connects this stop surface to the stop surface of the directly adjacent tooth. The second counting element 40 comprises a central hole 45 which is inserted on a second stud of the body 10 forming a second axis of rotation B, parallel to the first axis of rotation A, such that the second counting element 40 rotates on said second axis of rotation B. When it is associated with a third counting element 50, the second counting element 40 comprises a second cam 43, which can be formed by a radial projection, as can be seen in FIG. 12, and which is adapted to engage with the third counting element 50 upon each complete rotation, therefore every ten actuations in the example of the figures. The second counting element 40 engages with a first indexing tab 16 which engages with the second toothing 42. This first indexing tab 16 is mounted so as to pivot on the body 10, as can be seen, in particular, in FIGS. 19, 25 and 40. The first indexing tab 16 in particular aims to maintain the position of the second counting element 40 between two actuations, in order to guarantee a readable display in the viewing window 190. It can also act to prevent a rotation of the second counting element 40 in the direction opposite to that which is given to it by the first cam 33 of the first counting element 30.

Figure 13:
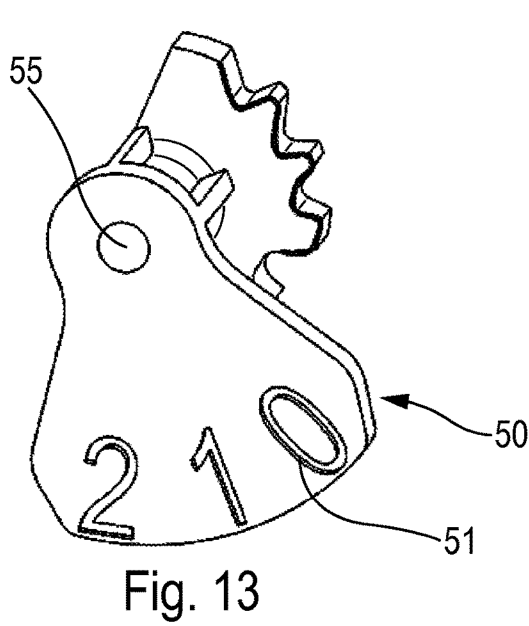
FIGS. 13 and 14 are perspective, schematic views of the hundreds wheel, respectively from the front and from the rear.
Figure 14:
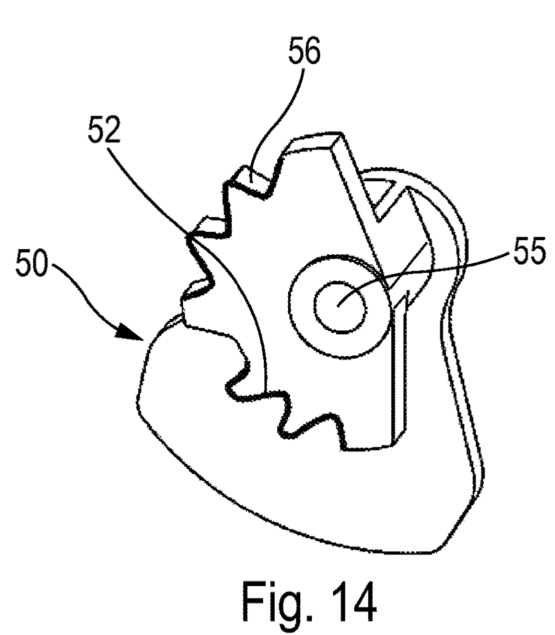

The third counting element 50, represented in detail in FIGS. 13 and 14, comprises on one side, third indication means 51 intended to be visible through the viewing window 190 of the counter, and on the other side, a third toothing 52 intended to engage with said second cam 43 of the second counting element 40 each time that the second counting element 40 has performed a complete rotation. In the example represented, the third counting element 50 is a hundreds wheel, and the third indication means 51 are therefore formed by the figures 0 to 2, for a counter adapted to count 200 doses. Likewise, the third toothing 52 only comprises a limited number of teeth defining recesses adapted to engage with said second cam 43. In the example represented, for a 200-dose counter, the third counting element only forms a wheel cross-section, which is advantageous from a size viewpoint of the counter and therefore dimension viewpoint of the device, but this is only one example of an advantageous embodiment. Advantageously, each tooth of the third toothing 52 comprises a stop surface and an inclined surface which connects this stop surface to the stop surface of the directly adjacent tooth. The third counting element 50 comprises a central hole 55 which is inserted on a third stud of the body 10 forming a third axis of rotation C, parallel to the first and second axes of rotation A and B, such that the third counting element 50 rotates on said third axis of rotation C. The third counting element 50 further comprises a fourth toothing 56, which engages with a second indexing tab 17 mounted so as to pivot on the body 10, as can be seen, in particular in FIGS. 20, 26 and 41. The second indexing tab 17 in particular aims to maintain the position of the third counting element 50 between two actuations, in order to guarantee a readable display in the viewing window 190. It can also act to prevent a rotation of the third counting element 50 in the direction opposite to that which is given to it by the second cam 43 of the second counting element 40. In a variant, indexing means could be provided, adapted to engage with the third toothing 52, which would make it possible to do without the fourth toothing.

FIGS. 15 to 41 illustrate a complete actuation cycle of the counter according to the advantageous embodiment represented in the drawings.

Figures 15, 16, 17, 18, 19, 20:
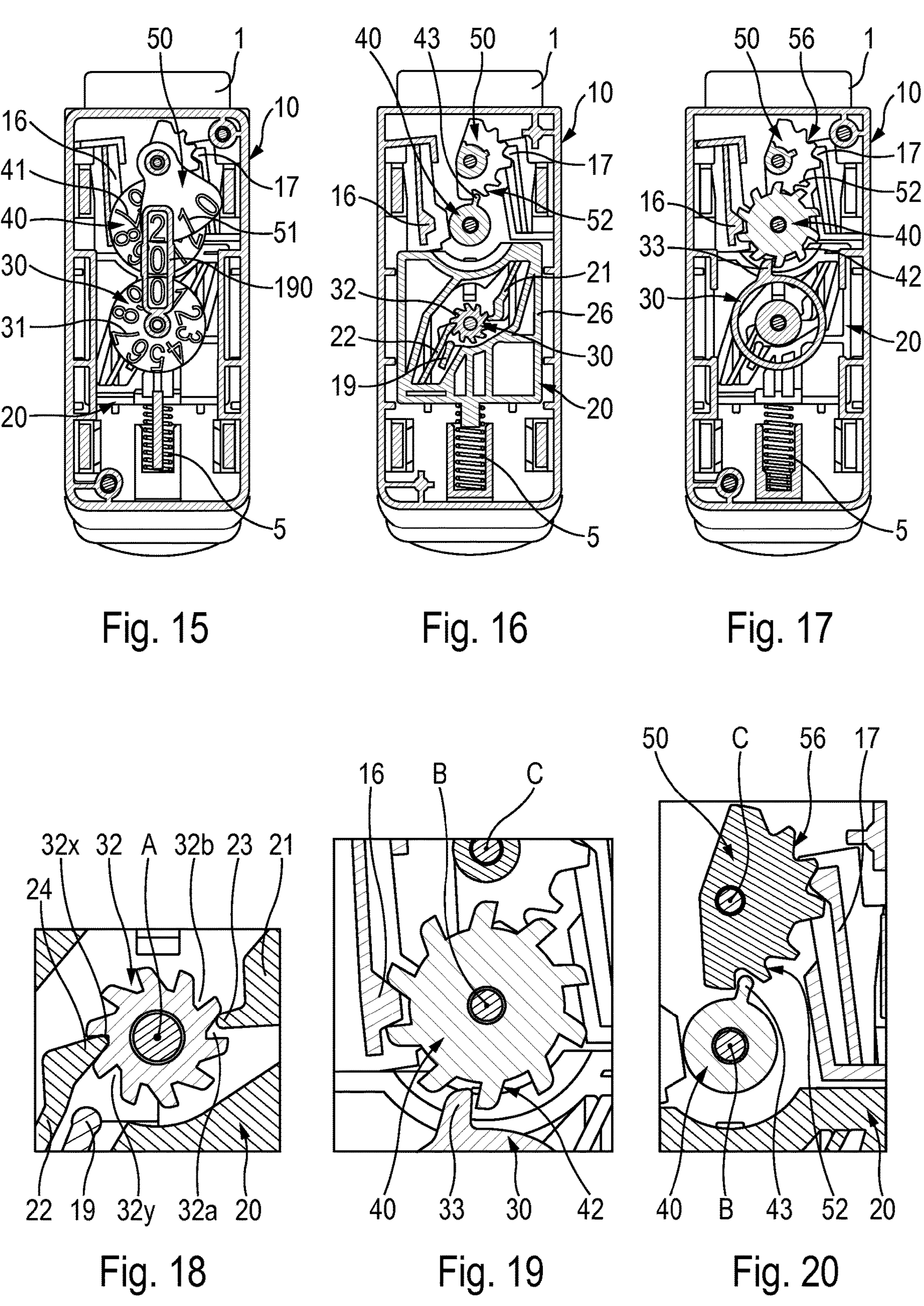
FIG. 15 is a cross-sectional, cutout, schematic view of the counter in the rest position, displaying the number 200.
FIG. 16 is a view similar to that of FIG. 15, along another cutting plane.
FIG. 17 is a view similar to that of FIGS. 15 and 16, also along another cutting plane.
FIGS. 18 to 20 are detailed views of the counter in the rest position.
Figures 36, 37, 38:
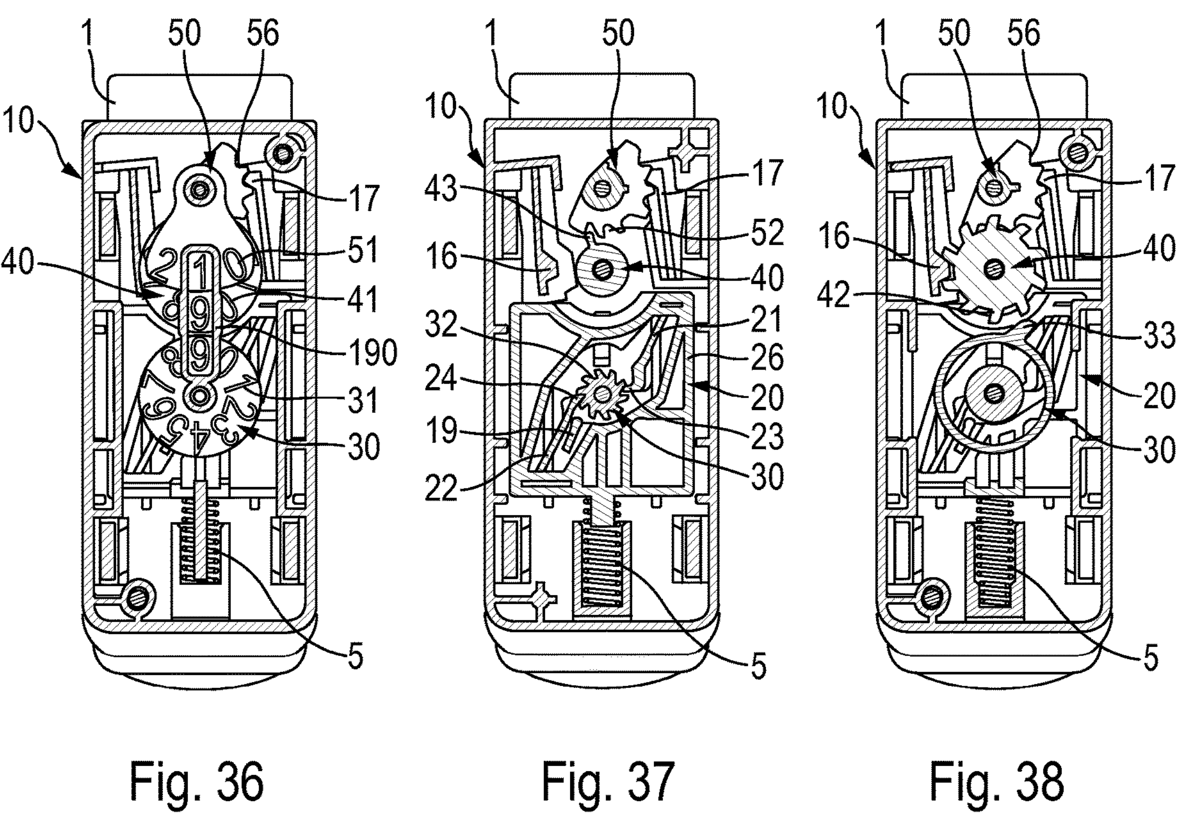
FIGS. 36 to 38 are views similar to those of FIGS. 15 to 17, at the end of the return stroke.
Figures 39, 40, 41:
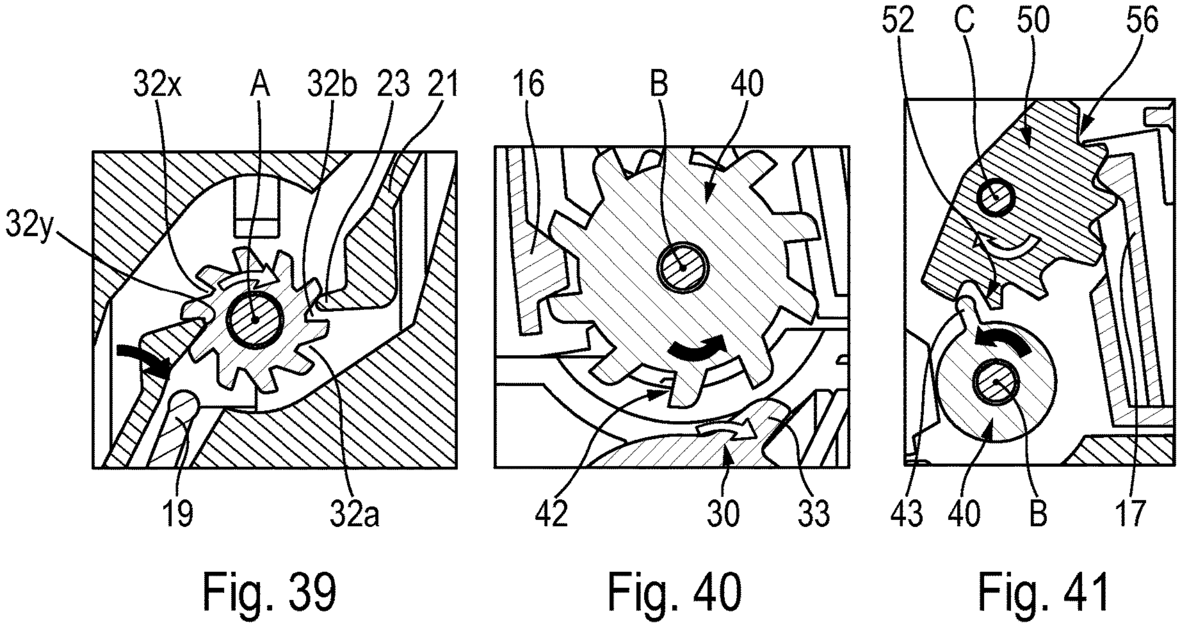
FIGS. 39 to 41 are views similar to those of FIGS. 18 to 20 at the end of the return stroke.

As can be seen in FIG. 15, the number 200 is displayed in the viewing window 190, and the actuation cycle which will be described is therefore that which will make the display of the counter pass from 200 to 199, i.e. a counter which displays the number of doses remaining to be dispensed and which will count from 200 to 0. Naturally, in a variant, the counter could count the number of doses dispensed, by counting from 0 to 200.

FIGS. 15 to 20 show the rest position of the counter, before actuation. In this rest position, the actuation element 20 is in the rest position, and the free end 23 of the first flexible tab 21 is in a first recess 32*a* of the first toothing 32 of the first counting element 30. Likewise, the free end 24 of the second flexible tab 22 is in another recess 32*x* of the first toothing 32 of the first counting element 30. Moreover, the first cam 33 of the first counting element 30 is in a recess of the second toothing 42 of the second counting element 40, and the second cam 43 of the second counting element 40 is in a first recess of the third toothing 52 of the third counting element 50. Finally, the first indexing tab 16 is disposed in a respective recess of the second toothing 42 of the second counting element 40, and the second indexing tab 17 is disposed in a respective recess of the fourth toothing 56 of the third counting element 50.

FIGS. 21 to 26 show the position of the counter during actuation. This position is that wherein the valve 2 is actuated to dispense a dose of the fluid product contained in the reservoir 1, and it is observed that the counter has already started to be actuated, before this dose dispensing. The user has moved the reservoir 1 axially in the body 10, which has caused the axial movement downward from the actuation element 20 with respect to the body 10. As can be seen in FIG. 24, the free end 23 of the first flexible tab 21 is pushed to the bottom of the first recess 32*a* of the first toothing 32 and rotates the first counting element 30 along the axis A in the counting direction. At the same time, the free end 24 of the second flexible tab 22 exits from the recess 32*x*, and the rotation of the first counting element 30 brings the following recess 32*y* to face said free end 24 of the second flexible tab 22. Simultaneously, the first cam 33 which rotates with the first counting element 30 rotates the second counting element 40 in its respective counting direction, with the first indexing tab 16 which is resiliently deformed radially outward to exit from its recess of the second toothing 42. Likewise, the second cam 43 which rotates with the second counting element 40 rotates the third counting element 50 in its respective counting direction, with the second indexing tab 17 which is resiliently deformed radially outward to exit from its recess of the fourth toothing 56.

FIGS. 27 to 30 show the position of the counter at the end of the actuation stroke. This position is that wherein the actuation stroke of the reservoir 1 and therefore of the actuation element 20 is continued after the dose dispensing position. It must be noted that this position is not essential to the operation of the counter, for which the actuation stroke could be stopped in the dose dispensing position of FIGS. 21 to 26. The actuation element 20 therefore arrives in the actuation position, with the first flexible tab 21 still in the recess 32*a* of the first toothing. The second flexible tab 22 is itself blocked radially by the stop element 19, which prevents it from deforming further radially inward. The stop element 19 is disposed radially inside and axially below said second flexible tab 22, in the position represented in FIG. 30. Thus, by descending axially, the second flexible tab 22 will be deformed radially outward, with the lower surface of the free end 24 of the second flexible tab 22 which slides over the stop element 19, while still being resiliently biased radially inward. This stop element 19 makes it possible to guarantee that the second flexible tab 2 will not be positioned two recesses farther, namely the recess 32*z* in FIG. 30, which would have the consequence of an over-counting, since the first counting element 30 would thus rotate by two increments instead of only one. As can be seen in FIG. 30, the free end 24 of the second flexible tab 22 is moved radially outward from the first toothing 32 by the stop element 19, and it cannot therefore be positioned in the recess 32*z*, while axially, it is located at this recess 32*z*. At the same time, the first and second indexing tabs 16, 17 return radially inward to be positioned in a next recess of their respective toothings 42, 56.

FIGS. 31 to 35 show the position of the counter during the return stroke. This position is that wherein the reservoir 1 and the actuation element 20 return from their respective actuation positions to their respective rest positions. The actuation element 20 raises to its rest position under the effect of the spring 5, with the first flexible tab 21, still in the recess 32*a* of the first toothing 32, which slightly rotates the first counting element 30 in the direction opposite the counting direction. This can, in particular, also be seen in FIG. 31, where it is seen that the FIG. 9 of the first counting element 30 is no longer exactly aligned in the viewing window 190 as was the case in FIG. 27. The second flexible tab 22 raises by sliding on the stop element 19, still by being resiliently biased radially inward. As can be seen in FIG. 34, the free end 24 of the second flexible tab 22 axially raises and moves radially inward to be positioned in the recess 32*y*, which is directly adjacent to it at the recess 32*x*, wherein it was at the start of the actuation cycle.

FIGS. 36 to 41 show the position of the counter at the end of the return stroke. This position is that wherein the reservoir 1 and the actuation element 20 are returned into their respective rest positions. It is observed that the viewing window 190 shows the number 199, with therefore a dose which has been counted during this complete actuation cycle. The actuation element 20 is raised into its rest position under the effect of the spring 5, with the free end 23 of the first flexible tab 21 which is deformed radially on the first toothing 32 to be snap-fitted in the second recess 32*b* directly adjacent to the first recess 32*a*. The second flexible tab 22 raises axially by pushing on the recess 32*y*, which continues the rotation of the first counting element 30 in the counting direction. This makes it possible for the first cam 33 to exit from the second toothing 42 of the second counting element 40. This will no longer move until the first cam 33 will have performed a complete rotation with the first counting element 30, corresponding to the counting of 9 additional doses. After this complete rotation, the first cam 33 will engage with the recess following the second toothing 42. Likewise, the second cam 43 exits from the third toothing 52 of the third counting element 50, and this will no longer move until the second counting element 40 has performed a complete rotation, corresponding to the counting of 99 additional doses. After this complete rotation, the second cam 43 will engage with the recess following the third toothing 52. The indexing tabs 16, 17 prevent not only the second and third counting elements 40, 50 from rotating in the direction opposite the counting direction, but they also react as centring elements to perfectly position and centre the indication means 41, 51 in the viewing window 190.

An advantage of the present invention is that the first flexible tab 21 is always in contact with the first toothing 32 of the first counting element 30. Thus, at rest, before an actuation, the free end 32 of the first flexible tab 21 is in a recess of the first toothing 32. Due to this, from the very start of the axial movement of the actuation element 20, the counter will be actuated, therefore always before the dose of fluid or powder product is dispensed, which guarantees that there can be no under-counting. Indeed, from the start of the actuation, the second flexible tab 22 exits from the first toothing 32 and is positioned facing the following recess, which guarantees a complete dose counting, even in case of incomplete actuation stroke for the reservoir 1.

Naturally, with respect to the description made above, the counter could be produced in a manner different to that represented. In particular, the shapes and positions of the first and second flexible tabs 21, 22 could be different, on the condition that the first flexible tab 21 is adapted to move the first counting element 30 in rotation in a counting direction and that then the second flexible tab 22 is adapted to move the same first counting element 30 in rotation in the same direction. Likewise, the shapes and positions of the first and second indexing tabs 16, 17 could be different. The same applies for the first, second and third counting elements 30, 40, 50.

Other modifications can also be considered for a person skilled in the art, without moving away from the scope of the present invention such as defined by the accompanying claims.

The invention claimed is:

1. A dose counter for a device for dispensing a fluid or powder product, comprising an actuation element and at least one first counting element provided with a first toothing defining a plurality of recesses, said actuation element being axially movable along an axis between a rest position and an actuation position, by being resiliently biased towards the rest position by a resilient element, said first counting element being mounted so as to rotate on a first axis of rotation perpendicular to said axis, said actuation element comprising two flexible tabs, a first flexible tab engaging with said first toothing to rotate said first counting element in a counting direction when said actuation element moves from the rest position to the actuation position, and a second flexible tab engaging with said first toothing to rotate said first counting element, also in said counting direction when said actuation element returns from the actuation position to the rest position, said first and second flexible tabs being disposed radially outside of said first toothing and being resiliently biased radially inward into contact with said first toothing, wherein said counter comprises a stop element engaging with said second flexible tab to limit its radial movement inward when said actuation element moves into and out of the actuation position.

2. The dose counter according to claim 1, wherein said stop element, during an actuation cycle of the counter, guides said second flexible tab from an initial recess to an immediately adjacent recess, by preventing said second flexible tab from passing directly into a non-adjacent recess, thus preventing an over-counting.

3. The dose counter according to claim 1, wherein said stop element is disposed radially inside and axially below said second flexible tab.

4. The dose counter according to claim 3, wherein said stop element is radially and axially inclined with respect to said axis of movement of said actuation element.

5. The dose counter according to claim 1, wherein said first and second flexible tabs each comprise a free end in the form of a tip or a tooth, oriented opposite.

6. The dose counter according to claim 1, further comprising a second counting element provided with a second toothing, said first counting element comprising a first cam engaging upon each complete rotation of said first counting element with said second toothing to rotate said second counting element.

7. The dose counter according to claim 6, wherein a first indexing tab engages with said second toothing to define and maintain the position of said second counting element between two actuations.

8. The dose counter according to claim 6, further comprising a third counting element provided with a third toothing, said second counting element comprising a second cam engaging upon each complete rotation of said second counting element with said third toothing to rotate said third counting element.

9. The dose counter according to claim 8, wherein a second indexing tab engages with a fourth toothing of said third counting element to define and maintain the position of said third counting element between two actuations.

10. The dose counter according to claim 8, wherein said first counting element is a units wheel, comprising first indication means formed by the figures 0 to 9 and a first toothing comprising ten recesses adapted to engage with said first and second flexible tabs of said actuation element, said second counting element is a tens wheel, comprising second indication means formed by the figures 0 to 9 and a second toothing comprising ten recesses adapted to engage with said first cam of said first counting element, and said third counting element is a hundreds wheel, comprising third indication means, in particular formed by the figures 0 to 2, and a third toothing comprising, in particular, three recesses adapted to engage with said second cam of said second counting element.

11. The dose counter according to claim 1, comprising a cover provided with a viewing window.

12. A device for dispensing a fluid or powder product comprising a reservoir, a dispensing member, mounted on said reservoir, and a body incorporating a dispensing orifice, said reservoir being axially movable in said body along an axis to dispense a fluid or powder product, wherein said device comprises a dose counter according to claim 1.

13. The device according to claim 12, wherein said counter is fixed laterally to said body, the actuation of said device being performed by an axial manual pressure of the user on the reservoir and the actuation of said counter being performed by said axial movement of said reservoir which engages with said actuation element of said counter.

14. The device according to claim 12, wherein a first part of the actuation cycle of the counter is performed before any dispensing of fluid or powder product, and a second part of the actuation cycle of the counter is performed after dispensing of fluid or powder product.

15. The device according to claim 12, wherein said first counting element rotates on a first axis of rotation, said second counting element rotates on a second axis of rotation and said third counting element rotates on a third axis of rotation, said axes of rotation being perpendicular to said axis of movement of said reservoir, said axes of rotation being formed by respective studs of said body.

16. The dose counter according to claim 12, wherein the dispensing member is a metering valve.

17. The dose counter according to claim 1, wherein the resilient element is a spring.

* * * * *